United States Patent [19]

Russo et al.

[11] Patent Number: 5,478,490
[45] Date of Patent: Dec. 26, 1995

[54] SHAMPOOS CONTAINING POLYGLYCERYL ESTERS

[75] Inventors: Thomas R. Russo, Andover, N.J.; Larry K. Hall, Nazareth, Pa.; Victor A. Landeryou, Warwick, N.Y.

[73] Assignee: Lonza Inc., Fair Lawn, N.J.

[21] Appl. No.: 271,207

[22] Filed: Jul. 5, 1994

Related U.S. Application Data

[63] Continuation of Ser. No. 21,249, Feb. 23, 1993, abandoned, which is a continuation-in-part of Ser. No. 879,888, May 7, 1992, abandoned.

[51] Int. Cl.$^6$ ............................. A61K 7/50; C11D 1/66; C11D 1/83; C11D 1/94
[52] U.S. Cl. ................. 252/153; 252/89.1; 252/173; 252/174.17; 252/541; 252/546; 252/548; 252/550; 252/551; 252/DIG. 13; 424/70.12; 424/70.19; 424/70.21; 424/70.24
[58] Field of Search ........................ 252/89.1, 174.17, 252/173, DIG. 13, 550, 551, 153, 548, 546, 541; 424/70.12, 70.121, 70.19, 70.21, 70.24

[56] References Cited

U.S. PATENT DOCUMENTS

| | | | |
|---|---|---|---|
| 3,936,391 | 2/1976 | Gabby | 252/356 |
| 4,454,113 | 6/1984 | Hemker. | |
| 4,741,858 | 5/1988 | Grote | 252/142 |
| 4,938,953 | 7/1990 | Pena | 252/550 |
| 5,130,056 | 7/1992 | Jakobson | 252/551 |

FOREIGN PATENT DOCUMENTS

| | | | |
|---|---|---|---|
| 0379658 | 8/1990 | European Pat. Off. | C11D 1/825 |
| 0486074 | 5/1992 | European Pat. Off. | A61K 7/00 |
| 62-27493 | 2/1987 | Japan. | |
| 62-29411 | 6/1987 | Japan. | |
| 62-29408 | 6/1987 | Japan. | |
| 63-145215 | 6/1988 | Japan | A61K 7/06 |
| 3-97791 | 4/1991 | Japan. | |
| 2140452 | 11/1984 | United Kingdom | A61K 7/08 |

*Primary Examiner*—Dennis Albrecht
*Attorney, Agent, or Firm*—Darby & Darby

[57] ABSTRACT

A shampoo formulation containing a polyglyceryl ester as the viscosity builder is disclosed. These polyglyceryl esters have the formula:

$$R^5OCH_2-CH(OR^4)-CH_2-(O-CH_2\,CH(OR^3)-CH_2)_n-O-CH_2-CH(OR^2)-CH_2OR^1$$

wherein n is from 4 to 14 and one or more R groups is an acyl group containing from 8 to 22 carbon atoms and the remaining R groups are hydrogen. Such shampoos may be formulated to meet the criteria for both baby and adult shampoos without the need of using ethylene oxide derivatives. By tailoring the polyglyceryl ester employed, a pearlescent appearance can be created and characteristics such as viscosity and clarity may be affected.

5 Claims, No Drawings

SHAMPOOS CONTAINING POLYGLYCERYL ESTERS

RELATED APPLICATION

This application is a continuation of application Ser. No. 08/021,249, filed Feb. 23, 1993, now abandoned, which, in turn, is a continuation-in-part of application Ser. No. 07/879,888, filed May 7, 1992, now abandoned.

BACKGROUND OF THE INVENTION

It is well known that shampoos, to be marketable, must meet certain stringent requirements in addition to their necessary detergent properties. These requirements are to some degree dependent on which of the two major areas of application they are to be used in. In one area, i.e., for baby shampoos, it is desirable that they have outstanding clarity, a controlled range of viscosity, extremely low irritability, and rapid foaming. In contrast, for adult formulations, opaque (even pearlescent) properties are favored, high viscosity is preferred, mildness (while still necessary) is a less stringent requirement, and conditioning qualities are sought.

It is well known that shampoos not irritating to the eyes can be formulated with certain ratios of ethoxylated anionic and amphoteric detergents in combination with other highly ethoxylated ingredients. Systems of this type are usually thickened with high molecular weight ethoxylated esters such as PEG 6000 distearate or PEG 80 sorbitan stearate. See U.S. Pat. No. 4,177,171. The use of the high molecular weight ethoxylated esters is especially desired in baby shampoos because of the importance of viscosity control and irritation reduction.

To achieve the desired viscosity, mild shampoos have been thickened with gums and polymers. In recent years cationic polymers, and especially cationic cellulosic gums, have been popular because they provide conditioning properties as well as viscosity. See U.S. Pat. No. 3,962,418. Unfortunately, the cationic polymers and gums are perceived as having irritation potential and are generally avoided in formulating very mild baby shampoos.

In yet another approach, U.S. Pat. No. 4,426,310 teaches that a mild shampoo can be thickened by selecting an optimum ratio of anionic and amphoteric detergents. Shampoos of this type usually contain high levels of ethoxylated nonionics such as Polysorbate 20 to achieve low irritation scores.

One drawback of formulations dependent on ethylene oxide derivatives is that these derivatives often contain 10 or more ppm of 1,4-dioxane, an impurity which has been identified as a carcinogen. Another drawback is dependence upon the use of PEG 6000 DS, an expensive ethoxylate-containing ester that is troublesome to both manufacture and handle because of its inherent high viscosity.

More recently, in U.S. Pat. No. 5,130,056, it is taught that $C_8$–$C_{18}$ fatty acid monoesters of diglycerol and/or $C_8$–$C_{16}$ fatty acid diesters of tetraglycerol are useful for washing agents, cleaning agents, and toiletries, including shower preparations, bubble bath preparations, liquid hand cleansers, and hair shampoos. While these materials meet dermatological and toxicological requirements and, further, are biodegradable, they have not been found satisfactory for building broad viscosity ranges to the extent desirable for commercial formulations.

In light of the foregoing, it is obviously desirable to formulate baby shampoos which are entirely free of ethylene oxide derivatives and adult shampoos devoid of high molecular weight ethoxylated esters.

BRIEF DESCRIPTION OF THE INVENTION

In accordance with the instant invention, it has now been discovered that certain high molecular weight polyglyceryl esters (PGEs) can be effectively used to achieve the desired viscosity in low- and mild-irritation shampoos. Based on the total shampoo formulation, from 1 to 10 wt. %, preferably from 1 to 3 wt. %, of the PGEs are used. The resultant shampoos, by selection of the appropriate PGE and control of the amount used, can be formulated with viscosities ranging from 200 cps to 8000 cps without the need of including ethylene oxide derivatives in the formulation. Generally the baby shampoos of the invention have from 10 to 25 wt. % solids, while the adult shampoos contain from 8 to 30 wt. %.

The specific viscosity desired, as is understood by those skilled in the art, is dependent on the end use application. It is generally accepted that baby shampoos have viscosities in the 600 cps to 2000 cps range, with 1000 cps to 1500 cps being the range of choice. Mild adult shampoos will often be formulated to fall in the 1000 cps to 8000 cps viscosity range and some family shampoos are thickened to the gel stage. The polyglyceryl esters of this invention are capable of producing viscosities which range from a few hundred to thousands of centipoise. For example, decaglyceryl monooleate, by varying the amount used, can build shampoo viscosities from 200 to 5000 cps in baby shampoo formulations and from 2000 cps to over 20000 cps with a desired range of 3000 cps to 8000 cps in typical adult formulations. As will be explained hereafter, the PGEs may also be used to obtain the lower viscosities used in baby shampoo formulations.

The polyglyceryl esters are ideal viscosity-building additives because they are extremely safe and mild. Not only are they free of 1,4-dioxane, but the derivatives up to and including the decaglyceryl esters are approved as food additives by the FDA. A further advantage is that they are available from safe renewable resources, namely, glycerin and fatty acids. These basic raw materials, in turn, can be obtained, if so desired, strictly from non-animal sources.

It has been further discovered that certain PGEs offer, in addition to viscosity building and control, other benefits such as pearlescence, formulation stabilization, and mild conditioning properties. Because of the multiplicity of these benefits, formulations may be prepared containing PGEs which markedly reduce the number of ingredients from as many as ten or twelve to as few as six or seven.

DETAILED DESCRIPTION OF THE INVENTION

The polyglyceryl esters of the subject invention may be represented by the following general formula:

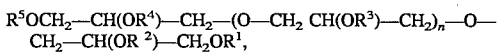

wherein R is hydrogen or an acyl group (R—CO—) of a fatty acid moiety having from 8 to 22 carbon atoms, the number of R groups is broadly from 1 to 14 and preferably from 1 to 12, and n is from 4 to 10.

The backbone is generally prepared by a condensation reaction which gives a normal distribution pattern in the final polymer. The average number of glycerin units in the base polyol will always total n+2. Generally, the polyglycerols used in the formulations of the invention have a molecular weight of from 300 to 1000, preferably from 500 to 800.

The fatty acid used to prepare the PGE can be selected from a broad range of structural types such as straight chain or branched and saturated or unsaturated. In some cases, the fatty acid chain length distribution will be a specific blend or will match that found in natural oils such as, for example, almond or sunflower oils. The preferred fatty acids have from 14 to 18 carbon atoms. The straight-chain 18-carbon acid is the most desirable.

In the case of baby shampoos, the polyglyceryl esters which provide the best viscosity building, while at the same time contributing to clear solutions, are based on hexa- to decaglycerols. The best performance was observed with the decaglyceryl series where approximately 10 moles of glycerin are reacted to form the polyglycerol moiety. The best combination of viscosity building and solubility is observed with monoesters. In such cases, if one R equals a fatty acid moiety, then the other Rs would be hydrogen. It will be understood that, in reality, the monoester material is not 100% but in the range of between 30% and 70% of the composition. The remainder, based on a statistical distribution, will be di-, tri- or higher esters along with some unreacted polyol. The R groups, in fact, represent a percentage ratio of fatty acid group to hydrogen. In the preferred case, the best performance is observed with the oleates, particularly decaglyceryl monooleate. Other useful PGEs include decaglyceryl dioleate, decaglyceryl monosunflowerate, and decaglyceryl monoalmond-ate.

In the case of adult shampoos, the n values may range from 4 (meaning a hexaglyceryl ester) to 10 (meaning a dodecaglyceryl ester). The best performance is obtained with compounds where n averages from 4 to 8, preferably from 4 to 6, and most desirable esters have an average n value of 4.

In the adult shampoos, clarity is less important than viscosity and conditioning effects. The PGEs can be used not only to develop viscosity and pearlescence, but also to provide other attributes to the shampoo such as conditioning benefits and formulation stability. These optimum benefits are achieved by adjusting the ratios of R to H in the PGE and by selecting an R group with the most appropriate carbon chain length distribution. Preferably, the R groups are straight-chain which have from 12 to 20 carbon atoms. Most desirably, the R groups have from 16 to 18 carbons. The n-stearate is particularly effective.

The total number of R groups depends on the size of the polyglycerol polymer. The n is broadly from 4 to 8, preferably from 4 to 6. For example, where n=4, the base polymer would be hexaglycerol and the total number of ester linkages (R groups) possible would be eight. To illustrate further, if the R groups derived from oleic acid are attached to a polyglycerol and n=8, the final product may have 12 ester units. The resultant compound would be decagtyceryl dodecaoleate. In adult type shampoos, the best results are observed with hexaglyceryl and dilaurate which contains 2 R groups having C-18 carbon chains. Other PGEs which may be used are decaglyceryl monostearate, octaglyceryl dilaurate, and hexaglyceryl monopalmitate and dipalmitate.

While the expression "adult shampoo" and "baby shampoo" are used above, it will be understood that the definitions of these formulations may indeed overlap. Also, while it is mandatory that baby shampoos be mild to achieve market acceptance, the adult shampoos of the invention may also have this attribute.

Essential components of all shampoos are surfactants. These may be selected from a wide variety of synthetic anionic, zwitterionic, and nonionic types. In mild- or low-irritation shampoos, the total anionic surfactant concentration will usually be minimized to the extent feasible.

Anionic Surfactants

The preferred anionic surfactants are the water-soluble salts of $C_{10}$ to $C_{14}$ fatty alcohol sulfates. These develop a rich foam. The sodium salts are most prevalent but other soluble salts include potassium, ammonium, diethanol- and triethanol-ammonium cations.

Sodium lauryl sulfate is most preferred. For a baby shampoo, the concentration range of the anionic on a 100% total formulation weight basis is in the range of from 1 to 5%, preferably from 1% to 3%. The best working level is between 2% and 2.5%. For an adult shampoo, from 5 to 20%, preferably from 8 to 18%, is used. The anionic concentration is minimized by a high loading of zwitterionic surfactants to the extent practical to help insure that its irritation potential is suppressed.

As a general matter, artionic surfactants are exemplified by the alkali metal salts of organic sulfuric reaction products having in their molecular structure an alkyl radical containing from 8 to 22 carbon atoms and a sulfonic acid or sulfuric acid ester radical (included in the term alkyl is the alkyl portion of higher acyl radicals). Preferred alkyl sulfates are sodium coconut oil fatty acid monoglyceride sulfate and sulfonates and those obtained by sulfating higher alcohols, i.e., those containing $C_8$ to $C_{18}$ carbon atoms. Other examples are sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; and water-soluble salts of condensation products of fatty acids with sarcosine.

Zwitterionic Surfactants

The zwitterionic surfactants make up the bulk of the low-irritation shampoo. The main ingredient is identified as cocamidopropyl betaine in the CTFA dictionary and the use level for a baby shampoo ranges from about 3 to about 10 wt. % on a 100% actives basis. The zwitterionic surfactants may be present in a range of about 3 to 10 wt. %. Betaines are preferred. The preferred range runs from approximately 4% to 9%. For an adult shampoo, the broad range is from 5 to 25%, with from 10 to 20% being preferred. Other alkylamidopropyl betaines can be used having alkyl groups derived from $C_{10}$ to $C_{16}$ fatty acids. The corresponding alkylamidopropyl sultaines are acceptable, especially cocamidopropyl sultaine.

Additional zwitterionic surfactants which can be used in the present invention are substituted imidazolines. The specific, preferred surfactants are described in the CTFA dictionary as sodium cocoamphoacetate and disodium cocoamphodiacetate. In addition to, or in place of, the coco-derived imidazolines, one can use similar structures prepared from $C_{10}$ to $C_{16}$ fatty acids. The active content of imidazoline surfactant, either as a single reagent or as a blend, runs from about 1.5% to about 2.5%. These materials do not have a critical impact on product performance, so a preferred use level is not necessary. The imidazoline surfactants are included in the shampoo development to provide irritation reduction (increase mildness) and to give some improvement in hair conditioning.

Zwitterionic surfactants are exemplified by derivatives of aliphatic quaternary ammonium, phosphonium, and sulfonium compounds, in which the aliphatic radicals are straight chain or branched, and wherein one of the aliphatic substituents contains from about 8 to 18 carbon atoms and one contains an anionic water-solubilizing group, e.g., carboxyl, sulfonate, sulfate, phosphate, or phosphonate. A general formula for these compounds is:

$$(R^3)_x$$
$$R^2 Y^{(+)} CH_2 R^4 Z^{(-)}$$

wherein $R^2$ is an alkyl, alkenyl, or hydroxyalkyl radical of from about 8 to about 18 carbon atoms. They may contain up to about 10 ethylene oxide moieties and up to 1 glyceryl moiety. Y is a nitrogen, phosphorus, or sulfur atom; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from about 1 to about 4 carbon atoms; and Z is a carboxylate, sulfonate, sulfate, phosphonate, or phosphate group.

EXAMPLES INCLUDE

4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradecoxylphosphonio]-2-hydroxyl-propane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxypentane-1-sulfate.

Examples of other betaines useful herein include the high alkyl betaines such as:
coco dimethyl carboxymethyl betaine,
lauryl dimethyl carboxymethyl betaine,
lauryl dimethyl alpha-carboxyethyl betaine,
cetyl dimethyl carboxymethyl betaine,
lauryl bis-(2-hydroxyethyl)carboxymethyl betaine,
stearyl bis-(2-hydroxypropyl)carboxymethyl betaine,
oleyl dimethyl gamma-carboxypropyl betaine,
lauryl bis-(2-hydroxypropyl)alpha-carboxyethyl betaine, etc.

The sulfobetaines may be represented by:
coco dimethyl sulfopropyl betaine,
stearyl dimethyl sulfopropyl betaine,
lauryl dimethyl sulfoethyl betaine,
lauryl bis-(2-hydroxyethyl)sulfopropyl betaine and the like. Amido betaines and amidosulfo betaines, wherein the $RCONH(CH_2)_3$ radical is attached to the nitrogen atom of the betaine, are also useful in this invention.

Amphoteric Surfactants

Examples of amphoteric surfactants which can be used in the compositions of the present invention are derivatives of aliphatic secondary and tertiary amines in which the aliphatic radical is straight chain or branched and wherein one of the aliphatic substituents contains from about 8 to about 18 carbon atoms and one contains an anionic water-solubilizing group, e.g., carboxy, sulfonate, sulfate, phosphate, or phosphonate. Examples of these compounds are sodium 3-dodecylaminopropionate, sodium 3-dodecylaminopropane sulfonate, and N-alkyltaurines such as the reaction product of dodecylamine and sodium isethionate, and N-higher alkyl aspartic acids.

Nonionic Surfactants

Nonionic surfactants, which are preferably used in combination with an anionic, amphoteric or zwitterionic surfactant, can be broadly defined as compounds produced by the condensation of a hydrophilic alkylene oxide group with an aliphatic or alkyl aromatic hydrophobic compound. Examples of preferred classes of nonionic surfactants are:

1. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, up to about 10 ethylene oxide moieties, and up to 1 glyceryl moiety, and $R_2$ and $R_3$ contain from 1 to about 3 carbon atoms and up to about 1 hydroxy group, e.g., methyl, ethyl, propyl, hydroxyethyl, or hydroxypropyl radicals. Examples of amine oxides suitable for use in this invention include:
dimethyldodecylamine oxide,
oleyldi(2-hydroxyethyl)amine oxide,
dimethyloctylamine oxide,
dimethyldecylamine oxide,
dimethyltetradecylamine oxide,
3,6,9-trioxaheptadecyldiethylamine oxide,
di(2-hydroxyethyl)tetradecylamine oxide,
2-dodecoxyethyldimethylamine oxide,
3-dodecoxy-2-hydroxypropyldi(3-hydroxypropyl)amine oxide, and
dimethylhexadecylamine oxide.

2. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, up to about 10 ethylene oxide moieties, and up to 1 glyceryl moiety and R' and R" are each alkyl or monohydroxyalkyl groups containing from 1 to 3 carbon atoms. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide, tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide, and
2-hydroxydodecyldimethylphosphine oxide.

3. Long chain dialkyl sulfoxides containing one short chain alkyl or hydroxy alkyl radical of 1 to about 3 carbon atoms (usually methyl) and one long hydrophobic chain which contains alkyl, alkenyl, hydroxy alkyl, or keto alkyl radicals containing from about 8 to about 20 carbon atoms, up to about 10 ethylene oxide moieties, and up to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Though not generally desirable as ingredients in the formulations of the invention, limited amounts of the following ethylene oxide derivatives may be used as the nonionic surfactant:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of straight or branched chain aliphatic alcohols having from 8 to 18 carbon atoms with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

In addition to the basic components described above, the present invention may contain a variety of optional ingredients which are generally used in shampoos. These include polyols, preservatives, silicon fluids, suspending agents, dyes, fragrances, preservatives, and buffering or pH control agents. For baby shampoos, such agents should be water-soluble to insure product clarity and not be irritating to skin or eyes.

Polyols

A further optional ingredient involves the addition of a polyol such as glycerin, propylene glycol, sorbitol or other cosmetically acceptable glycols. Polyols are added to provide auxiliary benefits such as secondary viscosity control, skin and hair moisturizing, bulking, or feel modification. In the shampoo products described below, glycerin was judged to be the best candidate to provide a better feel.

Preservatives

Preservatives include dimethyl dimethylolhydantoin (DMDMH), DMDMH/iodopropynyl-butyl carbamate (Glydant Plus, a registered trademark of Lonza Inc.), benzyl alcohol, methyl paraben, propyl paraben and imidazolidinyl urea. Of course, there are many additional preservatives that will function effectively in shampoos.

Buffering and pH-Control Agents

It is generally desirable to adjust mild shampoos such that the pH falls in the 5.5 to 7.5 range. In the formulations of the invention, the preferred pH range is 6.5 to 7.0. This can be adjusted, as needed, with either a base such as sodium hydroxide or sodium carbonate or an acid such as citric acid, succinic acid, or phosphoric acid.

Silicone fluids

Non-volatile silicones are the most suitable silicone fluids that may be used in the present compositions. The non-volatile silicone fluid may be either a polyalkyl siloxane, a polyaryl siloxane, a polyalkylaryl siloxane or a polyether siloxane copolymer and is present at a level of from about 0.1% to about 10.00%, preferably from about 0.5% to about 5.0%. Mixtures of these fluids may also be used. The dispersed silicone particles should also be insoluble in the shampoo matrix.

The essentially non-volatile polyalkyl siloxane fluids that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970. Preferably the viscosity ranges from about 350 centistokes to about 100,000 centistokes.

The essentially non-volatile polyalkylaryl siloxane fluids that may be used include, for example, polymethylphenyl siloxanes having viscosities of about 15 to 30,000 centistokes at 25° C. These siloxanes are available, for example, from the General Electric Company as SF 1075 methyl phenyl fluid or from Dow Corning as 556 Cosmetic Grade Fluid.

The essentially non-volatile polyether siloxane copolymer that may be used is, for example, a polypropylene oxide modified dimethyl polysiloxane (e.g., Dow Corning DC-1248), although ethylene oxide or mixtures of ethylene oxide and propylene oxide may also be used.

References disclosing suitable silicone fluids include the previously mentioned U.S. Pat. No. 2,826,551 to Geen; U.S. Pat. No. 3,964,500, Jun. 22, 1976, to Drakoff; U.S. Pat. No. 4,364,837 to Pader, and British Patent No. 849,433 to Woolston. All of these patents are incorporated herein by reference. Also incorporated herein by reference is *Silicon Compounds*, distributed by Petrarch Systems, Inc., 1984. This reference provides a very good listing of suitable silicone materials.

Another silicone material found especially useful in the present compositions to provide good dry combing is a silicone gum. Silicone gums are described by Petrarch and others, including U.S. Pat. No. 4,152,416, May 1, 1979, to Spitzer et al. and Noll, Walter, *Chemistry and Technology of Silicones*, New York: Academic Press, 1968. Also describing silicone gums are General Electric Silicone Rubber Product Data Sheets SE 30, SE 33, SE 54, and SE 76. All of these described references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

Optional Components

It has been discovered that PGEs provide multiple benefits such as thickening, pearlizing, suspending, stabilizing, and emulsification. In many cases, the PGEs can be used to replace all or part of gums and polymers that are used to develop viscosity. Certain PGEs can be used to replace ethylene glycol stearates where a pearl effect is desired. Other pearlizing agents may also be replaced. PGEs may be used in place of nonionic surfactants and xanthan and guar gums to provide suspension properties. Other optional materials are described below.

The suspending agent useful in the present compositions can be any of several long chain acyl derivative materials or mixtures of such materials. Included are ethylene glycol esters of fatty acids having from about 16 to about 22 carbon atoms. Preferred are the ethylene glycol stearates, both mono- and distearate, but particularly the distearate containing less than about 7% of the monostearate. Other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide, stearic monoisopropanolamide, and stearic monoethanolamide stearate. Other long chain acyl derivatives include long chain esters of long chain fatty acids (e.g., stearyl stearate, cetyl palmitate, etc.), glyceryl esters (e.g., glyceryl distearate), and long chain esters of long chain alkanol amides (e.g., stearamide DEA distearate, stearamide MEA stearate).

Still other suitable suspending agents are alkyl ($C_{16-22}$) dimethyl amine oxides such as stearyl dimethyl amine oxide. If the compositions contain an amine oxide or a long chain acyl derivative as a surfactant, the suspending function could also be provided and additional suspending agent may not be needed if the level of those materials are at least the minimum level given below.

The suspending agent is present at a level of from about 0.50% to about 5.0%, preferably from about 0.5% to about 3.0%. The suspending agent serves to assist in suspending the silicone material and may give pearlescence to the product. Mixtures of suspending agents are also suitable for use in the compositions of this invention.

Xanthan gum can also be used to suspend the silicone fluid. This biosynthetic gum material is commercially available and is a hetero-polysaccharide with a molecular weight of greater than 1 million. It is believed to contain D-glucose, D-mannose, and D-glucuronate in the molar ratio of 2.8:2.0:2.0. The polysaccharide is partially acetylated with a 4.7% acetyl. This and other information is found in Roy L. Whistler, Ed., *Industrial Gums—Polysaccharides and Their Derivatives* (New York: Academic Press, 1973). Kelco, a Division of Merck & Co., Inc. offers xanthan gum as Keltrol®. The gum is present at a level of from about 0.3% to about 3%, preferably from about 0.4% to about 1.2%, in the compositions of the present invention.

Cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride may also be added.

Supplemental thickeners and viscosity modifiers include sodium chloride, sodium sulfate, polyvinyl alcohol, and ethyl alcohol. Perfumes, dyes, and sequestering agents such as disodium ethylenediamine tetraacetate may also be used. Such agents generally are used individually at a level of from about 0.01% to about 10%, preferably from about 0.5% to about 5.0% by weight of the composition.

The examples below are given solely for the purpose of illustration and are not intended to limit the scope of the present invention. Many variations are possible without departing from the spirit and scope of the invention.

In the examples, deionized water is weighed into a suitable container and the anionic surfactant is mixed in gently to minimize foam and aeration. The betaine, the amphoteric surfactants, and the polyol are added with stirring in the order listed. The clear shampoo blend is heated and, when the temperature reaches between 70° C. and 75° C., the polyglyceryl ester is added. After the polyglyceryl ester is completely dissolved and the system is clear, the heat is discontinued and replaced with cooling. Preservatives, fragrance, and dyes are added when the batch has cooled to 45° C. or lower. When the batch returns to room temperature, compensation is made for evaporated water and the pH is adjusted to the 6.5 to 7.0 range.

Examples I and II compare a market-leading baby shampoo which is known to have a zero score in the Draize test and a harsh commercial shampoo which is irritating to the eyes.

EXAMPLE I

A clear, mild shampoo free of ethylene oxide adducts and thickened with polyglyceryl ester and having the following composition was prepared as described above.

| Components | Parts by Weight |
| --- | --- |
| Sodium lauryl sulfate | 6.00 |
| Cocamidopropyl betaine | 16.00 |
| Sodium cocoamphoacetate | 2.00 |
| Disodium cocoamphodiacetate | 2.00 |
| Glycerin | 2.50 |
| Decaglyceryl monooleate | 1.50 |
| Glydants ® Plus | 0.05 |
| Fragrance | 0.50 |
| Deionized water and dyes | 69.45 |

The pH was adjusted to 6.6 with citric acid. The viscosity, measured with a Brookfield instrument, Model RVT, was 1850 cps. Using the Organogenesis test, the cell viability after 5 minutes exposure was 81%. In contrast, the leading formulation of baby shampoo containing ethylene oxide derivatives had only a 73% cell viability, while a conventional adult shampoo scored 6%. This illustrates the mildness of the shampoo of the invention.

As a comparison, the decaglyceryl monooleate was omitted from the above formulation and the viscosity dropped to 1100 cps. This clearly demonstrates the thickening power of the PGE.

The non-irritating performance of the shampoos of the invention was demonstrated by in vitro methodology which was developed by organogenesis, Inc. of Cambridge, Mass., and is based on the use of cultured living cells which respond like human skin. In this test, one measures the percentage of cells that survive exposure to a foreign compound over a relatively short time period. The test results are not directly correlated to Draize eye test scores, but the degree of non-irritancy can be estimated by comparison with known materials.

EXAMPLE II

The ethylene oxide (EO) free product of Example I (1.5% PGE) and a similarly constituted product with 10% PGE were compared with the market leading baby and adult shampoos. The baby shampoo (J&J) is sold by Johnson & Johnson Consumer Products Inc., Spellman, N.J. This product contains water, PEG-80 sorbitan laurate, cocamidopropyl betaine, sodium trideceth sulfate, sodium chloride, lauroamphoglycinate, PEG-150 distearate, sodium laureth- 13 carboxylate, fragrance, citric acid, quaternium 15, tetrasodium EDTA, D&C yellow No. 10, and D&C orange No. 4. The adult shampoo is Prell®, sold by Procter & Gamble of Cincinnati, Ohio. It contains water, ammonium laureth sulfate, ammonium lauryl sulfate, glycol distearate, cocamide MEA, dimethicone, citric acid, sodium hydroxide, fragrances, EDTA, ammonium xylenesulfonate, ammonium chloride, methylchloroisothiazolinone, methylisothiazolinone, FD&C blue No. 1, and FD&C yellow No. 5.

The J&J baby shampoo is known to have a zero score in the Draize test. The Prell adult shampoo is characterized as harsh and is irritating to the eyes. The results are shown in Table I.

TABLE I

| Shampoo Sample (1% Concentration) | % Cell Viability (5 min. Exposure) |
| --- | --- |
| Baby shampoo (J&J) | 73 |
| EO-free shampoo (1.5% PGE)* | 81 |
| EO-free shampoo (10% PGE)* | 95 |
| Adult shampoo (Prell ®) | 6 |

* Decaglyceryl monooleate

The higher the level (%) of cell viability, the safer or more non-irritating the sample. The data in Table I demonstrate that PGEs, in this case decaglyceryl monooleate, have the ability to mitigate irritation.

EXAMPLE III

An additional clear, mild product containing no ethylene oxide adducts and most suitable for the baby shampoo market is described in the following table:

| Components | Parts by Weight |
| --- | --- |
| Sodium lauryl sulfate | 5.00 |
| Cocamidopropyl betaine | 11.00 |
| Sodium cocoamphoacetate | 3.00 |
| Disodium cocoamphodiacetate | 3.00 |
| Glycerin | 2.50 |
| Decaglyceryl monooleate | 1.50 |
| Glydant ® Plus | 0.05 |
| Fragrance | 0.50 |
| Deionized water and dyes | 73.45 |

The pH was adjusted to 6.6 with citric acid. The viscosity, measured with a Brookfield instrument, Model RVT, was 6100 cps. When the polyglyceryl ester was omitted, the viscosity of the Example III shampoo dropped to 4000 cps.

EXAMPLE IV

A "comb-out" study was conducted on hair tresses to determine performance properties of the EO-free baby shampoo (Example III). Three formulas of the invention were evaluated against the market leading baby shampoo (J&J). The ingredients which varied in the EO-free formulas were glycerine, sorbitol, and propylene glycol. The following procedure was used in preparing all hair tresses for evaluation:

(1) Rinse in lukewarm water.
(2) Comb wet, six times.
(3) Apply a measured amount of test shampoo.
(4) Lather and rinse.
(5) Comb wet, six times.
(6) Blow-dry and evaluate for tactile feel.

The results of the overall evaluation rated the three EO-free baby shampoos as being better in conditioning properties than the market leading baby shampoo. The improved hair feel was readily detectable and prevented a dry matte feel.

EXAMPLE V

This example demonstrates a mildly pearlescent 2-in-1 shampoo wherein the pearl effect is derived from hexaglyceryl distearate. The PGE also generates the high viscosity.

| Components | Parts by Weight |
| --- | --- |
| Ammonium lauryl sulfate | 30.00 |
| Ammonium laureth sulfate | 13.50 |
| Cocamonoethanolamine | 1.00 |
| Hexaglyceryl distearate | 3.00 |
| Dimethicone | 1.00 |
| Sodium chloride | 0.40 |
| Glydant ® Plus | 0.10 |
| Deionized water | 51.00 |

The pH was adjusted to 6.41 with citric acid. The viscosity, measured with the Brookfield viscometer, was 7200 cps.

COMPARATIVE EXAMPLE

The hexaglyceryl distearate was omitted from the product of Example V. As a result, the viscosity was much lower and the slight pearlescence was replaced with a hazy, somewhat translucent appearance.

| Components | Parts by Weight |
| --- | --- |
| Ammonium lauryl sulfate | 30.00 |
| Ammonium laureth sulfate | 13.50 |
| Cocamide monoethanolamine | 1.00 |
| Dimethicone | 1.00 |
| Sodium chloride | 0.40 |
| Glydant ® Plus | 0.10 |
| Deionized water | 54.00 |

The pH was adjusted to 6.38 with citric acid. The viscosity was cps as measured with the Brookfield viscometer. This is too low for a satisfactory adult shampoo.

EXAMPLE VI

A product evaluation panel test was conducted to compare the hair performance properties of the 2-in-1 shampoos of this invention against Pert Plus®, a leading conditioning shampoo. The term "2-in-1" is used to describe a product that contains both a shampoo and a conditioner. Pert Plus®, marketed as a "shampoo plus conditioner in one," contains water, ammonium lauryl sulfate, ammonium laureth sulfate, dimethicone, glycol distearate, ammonium xylenesulfonate, fragrance, cocamide MEA, tricetylmonium chloride, xanthan gum, cetyl alcohol, stearyl alcohol, sodium chloride, methylchloroisothiazolinone, methylisothiazolinone, sodium citrate, citric acid, D&C green No. 8, D&C yellow No. 10, and FD&C blue No. 1.

Thirty panelists evaluated three conditioning shampoos based on a "sequential monadic" test format. The panel was divided into two groups. The first fifteen panelists evaluated a 2-in-1 with silicone against the market leader. The second fifteen panelists evaluated a 2-in-1 with silicone against a 2-in- 1 without silicone, both containing PGEs. The length of the study was two weeks. Specific questionnaires were completed during the evaluation period.

The results of the test indicate that the 2-in-1 shampoo performs as well as the market leader in foaming, rinse off, and initial manageability to the hair. In comparing the 2-in-1 with and without silicone, the panelists detected conditioning properties in the non-silicone formula. This suggests that the PGE contributes a conditioning benefit. The incorporation of the PGE also produced the desired effects of pearlescence, viscosity enhancement, and conditioning properties to the shampoo.

We claim:

1. A clear and mild baby shampoo formulation which comprises:
   (a) from 1 to 3 wt. % of sodium or ammonium lauryl sulfate;
   (b) from 1 to 3 wt. % of decaglyceryl monooleate or monosunflower-ate ester.
   (c) from 3 to 10 wt. % of cocoamidopropyl betaine;
   (d) from 2 to 2.5 wt. % of glycerin, propylene glycol, or sorbitol; and
   (e) from 1.5 to 2.5 wt. % of a cocoamphoacetate, cocoamphodiacetate or mixtures thereof,
said formulation having a viscosity in the range of from 200 to 5,000 centipoise and a pH in the range of from 6.5 to 7.5.

2. The clear and mild shampoo formulation of claim 1 wherein the solids concentration is from 10% to 25%.

3. A mildly pearlescent shampoo formulation which comprises:
   (a) from 5 to 20 wt. % of a water-soluble salt of a $C_{10}$ to $C_{14}$ fatty alcohol sulfate or a sulfuric acid ester of the reaction product of 1 mole of a higher fatty alcohol and 1 to 12 moles of ethylene oxide;
   (b) from 1 to 3wt. % of hexaglyceryl distearate;
   (c) from 0.5 to 5 wt. % of a fatty acid alkanol amide; and
   (d) from 0.1 to 10 wt. % of a non-volatile silicone,
said formulation having a viscosity in the range of from 3000 to 8000 centipoise and a pH in the range of from 6.5 to 7.5.

4. The shampoo formulation of claim 3 wherein component (a) is sodium or ammonium lauryl sulfate, optionally, in admixture with sodium or ammonium laureth sulfate.

5. The shampoo formulation of claim 3 wherein the fatty acid alkanol amide is coco-monoethanolamide.

* * * * *